(12) United States Patent
Huang et al.

(10) Patent No.: US 11,766,563 B2
(45) Date of Patent: *Sep. 26, 2023

(54) NANOSECOND PULSED POWER SOURCES HAVING MULTI-CORE TRANSFORMERS

(71) Applicant: Pulse Biosciences, Inc., Hayward, CA (US)

(72) Inventors: Chaofeng Huang, San Jose, CA (US); Gregory P. Schaadt, Santa Clara, CA (US); Kenneth R. Krieg, Fremont, CA (US)

(73) Assignee: Pulse Biosciences, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/881,589

(22) Filed: Aug. 4, 2022

(65) Prior Publication Data

US 2022/0370801 A1 Nov. 24, 2022

Related U.S. Application Data

(63) Continuation of application No. 16/719,920, filed on Dec. 18, 2019, now Pat. No. 11,452,870.

(51) Int. Cl.
*H01F 27/28* (2006.01)
*A61N 1/36* (2006.01)
(Continued)

(52) U.S. Cl.
CPC ....... *A61N 1/36034* (2017.08); *A61N 1/0472* (2013.01); *H01F 27/24* (2013.01);
(Continued)

(58) Field of Classification Search
CPC ............... H01F 27/2823; H01F 27/24; H01F 2027/2833; H05K 2201/1003;
(Continued)

(56) References Cited

U.S. PATENT DOCUMENTS 3,614,694 A 10/1971 Koontz
5,019,719 A 5/1991 King
(Continued)

FOREIGN PATENT DOCUMENTS

GB 1269958 A 4/1972
WO WO2016/007960 A1 1/2016
WO WO2021/126917 A1 6/2021

OTHER PUBLICATIONS

Aguglia; Pulse Transformers Design for Magnet Powering in Particle Accelerators, IEEE 15th European Conference on Power Electronics and Applications; pp. 1-9; Sep. 2, 2013.
(Continued)

*Primary Examiner* — Sherman Ng
(74) *Attorney, Agent, or Firm* — Shay Glenn LLP

(57) ABSTRACT

Described herein are apparatuses and methods for applying high voltage, sub-microsecond (e.g., nanosecond range) pulsed output to a biological material, e.g., tissues, cells, etc., using a high voltage (e.g., MOSFET) gate driver circuit having a high voltage isolation and a low inductance. In particular, described herein are multi-core pulse transformers comprising independent transformer cores arranged in parallel on opposite sides of a substrate. The transformer cores may have coaxial primary and secondary windings. Also describe are pulse generators including multi-core pulse transformers arranged in parallel (e.g., on opposite sides of a PCB) to reduce MOSFET driver gate inductance.

25 Claims, 5 Drawing Sheets

(51) Int. Cl.
  *A61N 1/04* (2006.01)
  *H01F 27/24* (2006.01)
  *H03K 3/353* (2006.01)
  *H05K 1/18* (2006.01)

(52) U.S. Cl.
  CPC ......... *H01F 27/2823* (2013.01); *H03K 3/353* (2013.01); *H05K 1/181* (2013.01); *H01F 2027/2833* (2013.01); *H05K 2201/1003* (2013.01); *H05K 2201/10166* (2013.01); *H05K 2201/10545* (2013.01)

(58) Field of Classification Search
  CPC .......... H05K 2201/10166; H05K 2201/10545; H03K 3/57
  See application file for complete search history.

(56) References Cited

U.S. PATENT DOCUMENTS

| | | | |
|---|---|---|---|
| 6,326,177 | B1 | 12/2001 | Schoenbach et al. |
| 6,473,317 | B1 | 10/2002 | Simopoulos |
| 6,831,377 | B2 | 12/2004 | Yampolsky et al. |
| 6,974,905 | B2 | 12/2005 | Kazama |
| 8,000,813 | B2 | 8/2011 | Schoenbach et al. |
| 8,512,334 | B2 | 8/2013 | Nuccitelli et al. |
| 8,822,222 | B2 | 9/2014 | Beebe et al. |
| 8,847,656 | B1 | 9/2014 | A et al. |
| 9,101,764 | B2 | 8/2015 | Nuccitelli et al. |
| 9,724,155 | B2 | 8/2017 | Nuccitelli et al. |
| 10,252,050 | B2 | 4/2019 | Kreis et al. |
| 10,850,095 | B2 | 12/2020 | Ebbers et al. |
| 11,167,125 | B2 | 11/2021 | Moss et al. |
| 11,452,870 | B2 | 9/2022 | Huang et al. |
| 2008/0304292 | A1 | 12/2008 | Zeng et al. |
| 2010/0182814 | A1 | 7/2010 | Tada et al. |
| 2011/0085362 | A1 | 4/2011 | Bordin |
| 2011/0092973 | A1 | 4/2011 | Nuccitelli et al. |
| 2011/0133835 | A1 | 6/2011 | Castaneda et al. |
| 2012/0050999 | A1 | 3/2012 | Cooper et al. |
| 2013/0003424 | A1 | 1/2013 | Song et al. |
| 2013/0076406 | A1* | 3/2013 | Xu .................. H03K 17/161 327/109 |
| 2014/0364797 | A1 | 12/2014 | Schoenbach et al. |
| 2015/0201991 | A1 | 7/2015 | Zemlin |
| 2016/0072393 | A1* | 3/2016 | McIntyre ............ H02M 3/1582 363/21.1 |
| 2017/0245928 | A1 | 8/2017 | Xiao et al. |
| 2018/0078755 | A1 | 3/2018 | Kreis et al. |
| 2020/0128688 | A1 | 4/2020 | Jin et al. |

OTHER PUBLICATIONS

Akemoto et al.; Development of the pulse transformer for NLC klystron pulse modulator; IEEE Particle Accelerator Conference; vol. 1; pp. 1322-1324, May 16, 1997.

Akemoto et al.; Pulse transformer R&D for NLC klystron pulse modulator; Digest of Technical Papers; 11th IEEE International Pulsed Power Conference; vol. 1; pp. 724-729; Jun. 29, 1997.

Bortis et al.; Design procedure for compact pulse transformers with rectangular pulse shape and fast rise times. IEEE transactions on Dielectrics and Electrical Insulation; 18(4); pp. 1171-1180; Aug. 11, 2011.

Chen et al.; An all-solid-state microsecond-range quasi-square pulse generator based on fractional-turn ratio saturable pulse transformer and anti-resonance network; Review of Scientific Instruments; 88(3): 034701; doi 10.1063/1/1.4977219; 8 pages; ; Mar. 2017.

Grebennikov; Power combiners, impedance transformers and directional couplers; High Frequency Electronics; 6(12); pp. 20-38; Dec. 1, 2007.

International Search and Written Opinion dated April Apr. 13, 2021 for PCT/US2020/065231; 16 pages.

Kolar et al.; Design Procedure for Compact Pulse Transformers with Rectangular Pulse Shape and Fast Rise Times; IEEE Transactions and Dielectrics and Electrical Insulation: 18(4); pp. 1171-1180; Aug. 1, 2011.

Pappas et al.; High Current Coaxial Pulse Transformer for Railgun Applications; Army Armament Research and Development Center; EM Launch Research: IEEE 5th Puulsed Power Conference; Jun. 10, 1985.

Zielinski et al.; Pulsed Current Transformer for Low Inductive Loads; Army Ballistic Research Lab Aberdeen Proving Ground MD; Oct. 1, 1987.

* cited by examiner

NANOSECOND PULSED POWER SOURCES HAVING MULTI-CORE TRANSFORMERS

CROSS REFERENCE TO RELATED APPLICATIONS

This application is a continuation of U.S. patent application Ser. No. 16/719,920, filed Dec. 18, 2019, titled "NANOSECOND PULSED POWER SOURCES HAVING MULTI-CORE TRANSFORMERS," now U.S. Patent Application Publication No. 2021/0187292 which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are pulsed power sources that include parallel, multi-core pulse transformers for MOSFET gate drivers. These apparatuses (systems and devices) generally relate to high voltage, sub-microsecond (e.g., nanosecond, picosecond, etc.) pulsing. In particular, described herein are nanosecond pulsing systems and apparatuses capable of delivering a high voltage, nanosecond pulsed electrical fields (nsPEF) for electrotherapy using parallel, multi-core (e.g., two or more core) pulse transformers.

BACKGROUND

A "nanosecond pulsed electric field" (nsPEF) may be applied for medical and/or therapeutic purposes, including in particular for the treatment of biological materials (e.g., cells and tissues). NsPEF may include an electrical field with a pulse width that may be less than about 1000 nanosecond (ns), such as between about 0.1 ns and 1000 ns, and may have peak voltages that are high voltage, in some variations as high as about 1 kV/cm, 2 kV/cm, 3 kV/cm, 4 kV/cm, 5 kV/cm, about 10 kV/cm, about 20 kV/cm, about 50 kV/cm, about 100 kV/cm, about 250 kV/cm, or about 500 kV/cm. Such high voltage, very brief pulses present unique problems for therapeutic medical devices. In particular, the delivery of rapidly changing (e.g., nanosecond or faster pulses) at high voltage may require very rapid MOSFET response times, requiring low MOSFET gate driver circuit inductance.

Therefore, it is desirable to provide devices and apparatuses, including systems for nanosecond pulsed electrical field generation and delivery that are configured to provide sub-microsecond (e.g., nanosecond) pulses, including pulses of 100 ns or less, that have fast output pulse rise times and falling times, that may also be pulsed with short delay times. Such apparatuses and methods will be particularly useful in the growing field of therapeutic nsPEF, including for medical treatments, including treatments of cancer/tumors, skin disorders and other applications.

SUMMARY OF THE DISCLOSURE

Described herein are apparatuses (systems, devices, etc.), and methods configured to apply high voltage, sub-microsecond (e.g., nanosecond range) pulsed output to a biological material, e.g., tissues, cells, etc., with very fast output pulse rise time and fall times.

Some of the apparatuses and methods described herein may be configured for delivering nanosecond pulsed electrical energy and may include, for example, one or more MOSFET drivers, one or more MOSFETs, and a plurality of parallel pulse transformers each comprising an independent transformer core wherein a plurality of primary and secondary windings are wrapped around each core. The primary and secondary windings may be coaxial relative to each other. Each of the one or more MOSFET drivers may be connected in parallel to the primary windings, and wherein each of the one or more MOSFETs are connected in parallel to the secondary windings.

For example, described herein are apparatuses for delivering sub-microsecond pulsed electrical energy that include two or more (e.g., dual-core, multi-core, etc.) pulse transformers having a high voltage isolation and a low circuit inductance, coupling one or more high voltage switches drivers (e.g., MOSFET drivers) to one or more high voltage switches (e.g., MOSFETs). In particular, described herein are sub-microsecond pulse generators that include HV switch driver circuits including one or more (and particularly two) pulse transformers as described herein, in which the two (or more) cores are independent of each other and are each wound with two or more cables forming the primary and secondary windings that may be arranged in parallel, with the primary connected to the HV switch driver(s) and the secondary connected to the HV switch/gate(s). The pulse transformers may be arranged in parallel; in some advantageous variations on opposite sides of the substrate holding the HV switch circuitry.

The sub-microsecond (e.g., nanosecond) pulse generator may be, for example, a tunable, high-voltage, sub-microsecond pulse generator based on a Marx-Switch stack hybrid circuit, having a plurality of different stages that each include, at each stage, a stack of power HV switches that allow relatively high charging voltages at each stage, permitting an overall output voltage with a single trigger. For example, see U.S. application Ser. No. 15/148,334 (publication no. US20170245928A1, titled "High-voltage analog circuit pulser with feedback control"), herein incorporated by reference in its entirety.

For example, the sub-microsecond pulse generator may be configured to provide at least a 200 kV/µs high voltage, high-current pulsed output. The high voltage (in some variations, high current) pulsed output generated by the sub-microsecond pulse generator may be, for example, configured to have a voltage of greater than 15 kV and an output current of greater than 300 A.

The apparatuses described herein may be configured to operate with a pulse delivery output that is configured to deliver the high voltage, high current, nanosecond pulses to a biological tissue. For example, the pulse delivery output may comprise a handpiece configured to deliver the high voltage pulsed output. In some variations, the handpiece may include a removable tip having a plurality of tissue-penetrating electrodes. For example, any of the handpieces as described in U.S. patent application Ser. No. 16/247,469 ("TREATMENT TIP WITH PROTECTED ELECTRODES"), filed on Jan. 14, 2019, and incorporated by reference in its entirety herein, illustrate examples of handpieces having removable tips that may be used. A handpiece may be used to deliver therapeutic energy to treat a tissue (e.g., skin, tumor, etc.) in a living subject (e.g., in vivo) or in tissue removed from a subject (e.g., ex vivo).

In some variations the apparatus may include a pulse delivery output that is configured as a cuvette (e.g., a cuvette fixture) or chamber for delivering high voltage nanosecond pulses. These apparatuses may be used with isolated portions of biological material, including extracted and/or cultured cells. For example, these apparatuses and methods may be used for electroporation.

Also described herein are methods of using any of the apparatuses described herein to apply high voltage nanosecond pulsing from a pulse generator. These methods may be methods for delivering the high voltage (in some cases high current) nanosecond pulses to a patient. For example, any of the apparatuses described herein may be used as part of a method of delivering nanosecond pulsed electrical energy to a biological material (such as a patient's tissue). In some variations, the method may alternatively include delivering the pulse output from a pulse delivery output that includes a cuvette chamber, e.g., to electroporate isolated tissue and/or cells.

The high voltage, high current, pulsed output may have, e.g., a voltage of at least 200 kV/μs.

For example, described herein are apparatuses for delivering sub-microsecond pulsed electrical energy including a pulse transformer. These apparatuses may include: one or more high voltage switch drivers; one or more high voltage switches; and one or more multi-core pulse transformers, wherein each multi-core pulse transformer comprises a first transformer core and a second (or more) transformer core that are arranged in parallel between the one or more high voltage switches drivers and the one or more high voltage switches, wherein the first transformer core and the additional transformer core(s) each include one or more cables (in some variation, coaxial cables) forming primary and secondary windings; further wherein the one or more high voltage switch drivers are coupled to the primary windings and the one or more high voltage switches are coupled to the secondary windings.

In any of these apparatuses, the first transformer and the second (or more) transformer may be symmetrically arranged in parallel between the one or more high voltage switches drivers and the one or more high voltage switches.

In general, the one or more high voltage switches may be MOSFETs and the one or more high voltage switch drivers may be MOSFET drivers. Other transistors (e.g., field-effect transistors) may be used.

For example, described herein are apparatuses (e.g., including a pulse transformer) for delivering sub-microsecond pulsed electrical energy comprising: one or more MOSFET drivers on a substrate; one or more MOSFETs on the substrate; and a parallel multi-core pulse transformer comprising a first transformer core and a second, independent, transformer core, wherein a plurality of coaxially arranged primary and secondary windings are wrapped around each of the first and second transformer cores, wherein the first transformer core is on a first side of the substrate and the second transformer core is on an opposite side of the substrate; further wherein each of the one or more MOSFET drivers is connected in parallel to the primary windings, and wherein each of the one or more MOSFETs are connected in parallel to the secondary windings.

In any of these apparatuses, the primary and secondary windings may be coaxially arranged relative to each other.

The one or more MOSFET drivers may be coupled to the primary windings so that each primary winding is electrically parallel, and wherein the one or more MOSFETs are coupled to the secondary windings so that each secondary winding is electrically parallel.

In general, the apparatus first core may be independent from the second core (e.g., electrically independent). In some variations the first core is separated from the second core by the substrate (e.g., the printed circuit board, PCB). In general, the first core may be arranged symmetrically between the high voltage gate/switch (e.g., MOSFET) and the high voltage gate/switch (e.g., MOSFET) driver. For example, the first core may be arranged on a first side of a printed circuit board (PCB) to which the one or more MOSFET drivers and one or more MOSFETs are attached, and the second core may be arranged on a second side of the PCB opposite from the first side.

In some variations for each transformer core, the plurality of coaxial cables are wound between 1 and 5 times around.

Any number of high voltage date/switches (e.g., MOSFETS) may be used. For example, the one or more MOSFETs may comprises a plurality of MOSFETs; the one or more MOSFET drivers comprises a plurality of MOSFET drivers.

Also described herein are pulse generators using any of these pulse transformers. For example, a sub-microsecond pulse generator comprising a pulse transformer as described above may be configured to provide at least a 200 kV/μs high voltage pulsed output. The pulse generator may include a handpiece configured to deliver the high voltage pulsed output. The handpiece may include a removable tip having a plurality of tissue-penetrating electrodes. The high voltage pulsed output generated by the sub-microsecond pulse generator may be configured to have a voltage of 1 kV or greater (e.g., in some variations, preferably 5 kV or greater, preferably 10 kV or greater, preferably 15 kV or greater, etc.) and an output current of 20 A or greater (e.g. preferably 50 A or greater, preferably 100 A or greater, preferably 200 A or greater, more preferably 300 A or greater, etc.).

For example, described herein are apparatuses for delivering sub-microsecond pulsed electrical energy that may include: one or more MOSFET drivers; one or more MOSFETs; and one or more multi-core pulse transformers, e.g., a dual-core pulse transformer, wherein each dual-core pulse transformer comprises a first transformer core and a second transformer core that are arranged in parallel between the one or more MOSFET drivers and the one or more MOSFETs so that the first transformer core is on a first side of a substrate and the second transformer core is on a second side of the substrate in parallel with the first transformer core; further wherein the one or more MOSFET drivers are coupled to a primary winding from each of the first and second transformer core, and the one or more MOSFETs are coupled to a secondary winding from each of the first and second transformer core. The one or more MOSFET drivers may be coupled to the primary windings so that each primary winding is electrically parallel, and wherein the one or more MOSFETs are coupled to the secondary windings so that each secondary winding is electrically parallel.

Although many of the examples described herein are dual-core pulse transformers having a first core and a second core that are independent and arranged in parallel, it should be understood that more than two cores may be used and arranged as described herein. Thus, the methods and apparatuses for reducing inductance (and increasing MOSFET drive current due to keeping each core below saturation) by paralleling two independent cores (e.g., dual-cores) can be extended to more than two cores.

Further, although the examples described herein include primary and secondary windings that are coaxially related to each other, this is not necessary. Coaxially arranged primary and secondary windings may further lower leakage inductance and therefore enhance the current transfer across the transformers described herein. For example, in some variations, the secondary windings may be coaxially arranged over the primary windings (or vice versa). The one or more MOSFETs may comprises a plurality of MOSFETs, and/or the one or more MOSFET drivers may comprise a plurality of MOSFET drivers. As mentioned above, a sub-microsecond pulse generator may include a pulse transformers wherein high voltage pulsed output generated by the sub-microsecond pulse generator is configured to have a voltage of greater than 5 kV and an output current of greater than 200 A.

Also described herein are methods of generating a sub-microsecond pulsed output, the method comprising: emitting a driving pulse from a high voltage switch driver to a multi-core pulse transformer through a primary winding of a first transformer core and a primary winding of a second transformer core, wherein the first and second transformer cores are arranged in parallel (e.g., in some variations on either sides of a substrate); and receiving the driving pulse at a high voltage switch from a secondary winding (for example, coaxially arranged relative the primary winding around the first transformer core and the second transformer core); wherein the driving pulse is a sub-microsecond driving pulse.

The high voltage switch may be a MOSFET and the high voltage switch driver may be a MOSFET driver. The MOSFET, MOSFET driver and first transformer core may be on a first side of a substrate (e.g., PCB), and the second transformer core may be on a second side of the substrate directly opposite from the first transformer core. The driving pulse may be emitted through a plurality of primary windings that are arranged in parallel. The primary windings and the secondary windings may be formed by a plurality of lengths of coaxial cable wrapped around the first transformer core and the second transformer core. Each of the first transformer core and the second transformer core may be wrapped by a plurality of lengths of coaxial cable.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

In general, the methods and apparatuses (e.g., devices, systems, etc.) described herein for pulsed power systems parallel, multi-core pulse transformers for high voltage (HV) switch drivers that are configured to provide very rapid on/off switching of the HV switch driver circuit(s) while preserving sharp rise time and fall times, e.g., when pulsing at sub-microsecond (e.g., nanosecond, including 1000 ns or less, 100 ns or less, etc.) output pulsing. In general, the HV switches described herein may be any high voltage switch/gate, such as transistors (e.g., field-effect transistors), including MOSFETs (driven by MOSFET gate driver circuits). These high voltage switches may be referred to herein for convenience as MOSFETs.

These methods and apparatuses may include small core/transformers arranged in multi-core configurations in which the pulse transformers are compact and configured in parallel to lower HV switch driver circuit inductance. This will allow the HV switch/gate(s), for example, the MOSFET(s) to be turned on/off fast (e.g., in the nanosecond range or less), and will also allow the HV switch turn on and turn off delay time to be correspondingly fast and may further provide faster load arcing protection.

Although the methods and apparatuses are described in the context of a sub-microsecond pulse generator for applying high voltage, sub-microsecond (e.g., nanosecond range) pulsed output to a biological material, e.g., tissues, cells, etc., these methods and apparatuses (including in particular the pulse transformer configurations described herein, may be used with or as part of any HV switch driver circuit that uses a pulse transformer.

Figure 1:
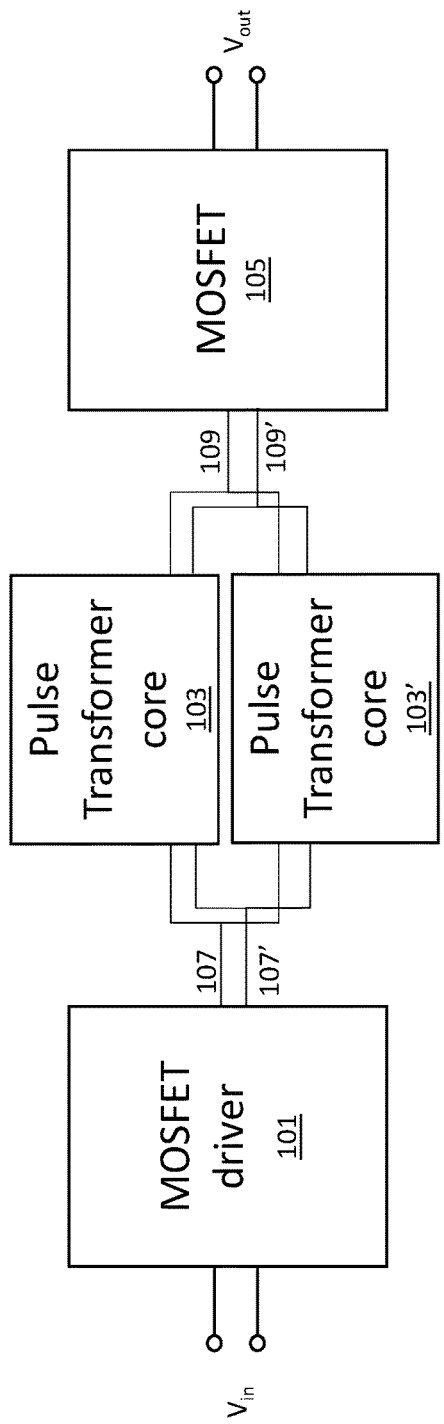
FIG. 1 is a schematic of one example of a portion of a pulse generator including a pair of parallel pulse transformers as described herein.

Further, the transformers (cores) described herein may be configured as low-power pulse transformers that typically reduce the inductance of the coupling from the HV switch (e.g., MOSFET) driver circuit to the HV switch (e.g., MOSFET transistor or power switch), as illustrated in the schematic of FIG. 1. In FIG. 1, the pulse transformer portion of a pulse generator is shown schematically, illustrating the driver (HV switch driver, shown in this example as a MOSFET driver 101) connected via the primary windings to a pair of parallel transformers 103, 103' that is in turn connected via the secondary windings to the HV switch/gate(s) (shown in this example as MOSFETs 105).

The transformers may include a single core with multiple parallel windings on the same core, or more preferably multiple cores that are arranged in parallel and/or symmetrically between the HV switch/gate(s) and HV switch driver(s). The multiple parallel windings may be made using a coaxial arrangement of the primary and secondary windings. Thus, the primary and secondary winding may be formed of a coaxially arranged cable in which, e.g., the primary windings are coaxially arranged over the secondary winding (alternatively, in some variations the secondary winding may be coaxially arranged over the primary winding). A single core with multiple parallel windings on the same core will saturate the core, as the saturation depends on the total coupled flux of the windings to the core.

Figure 2A:
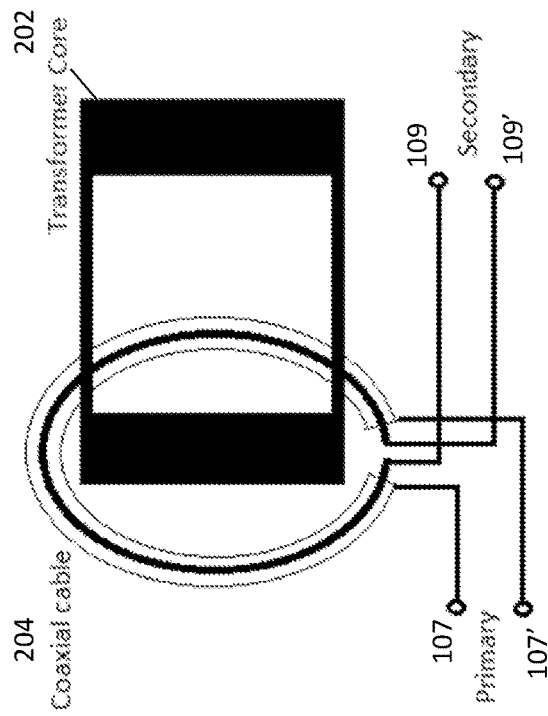
FIG. 2A is one example of a pulse transformer using a coaxial cable as primary and secondary as described herein.

FIG. 2A schematically illustrates one example of a transformer in which a transformer core 202 is wrapped by a coaxial cable 204 in which the primary winding 107, 107' is coaxially arranged around the secondary winding 109, 109'. The coaxial arrangement shown in FIG. 2 is a single core with a single winding on the core. The use of coaxial cable for the primary and secondary windings may lower the leakage inductance. In some variations, two or more turns of the transformer primary and secondary can be used. In FIG. 2A, a single turn of the coaxially arranged primary and secondary windings is shown. In some variations more than one (e.g., 2, 3, 4, 5, between 1 and 10, between 1 and 7, between 1 and 5, less than 5, etc., including half turns such as 1.5, 2.5, 3.5, etc.) may be used. Alternatively or in addition, in some variations a single core may be wrapped with multiple coaxial cables arranged in parallel, as shown in FIG. 2B.

Figure 2B:
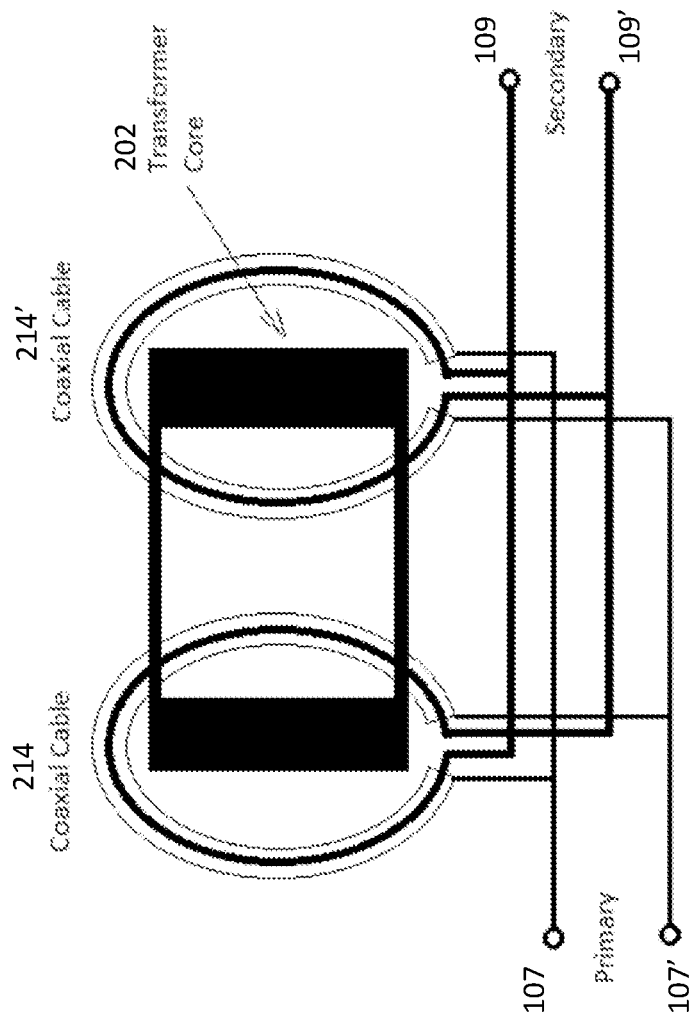
FIG. 2B is an example of a pulse transformer using two coaxial cables in parallel as the primary and secondary windings as described herein.

In FIG. 2B, the pulse transformer may include two coaxial cables 214, 214' arranged in parallel on the transformer core 202. Each coaxial cable is shown with a single turn in this example. In some variations more than 1 turn (e.g., 1.5, 2, 2.5, 3, 3.5, etc.) may be used, as mentioned above. Alternatively or additionally, additional length of coaxial cable may be arranged in parallel around the core, for a total of 2, 3, 4, 5, 6, etc. lengths or coaxial cables in which the primary windings 107, 107' are arranged in parallel with each other (e.g., each receiving the primary input, and the primary output) and coaxially around secondary windings 109, 109'; each secondary winding is arranged in parallel (e.g., receiving the same secondary input and the same secondary output). The variation shown in FIG. 2B may result in substantially lower inductance, e.g., by including two or more coaxial cables for the parallel primary and secondary windings on each transformer of a pulse transformer.

In some variations the core saturation may be improved by adding multiple cores in parallel, rather than multiple windings per core. Thus, the incorporation of independent (not magnetically coupled) cores with parallel windings may allow a higher drive current without saturating the cores and, by having more than one circuit in parallel, may reduce the inductance between the driver and the HV switch (e.g., MOSFET), or driven switching element. For example, FIGS. 3 and 4 show multiple, independent cores arranged in parallel.

The pulse transformers described herein may be used as part of (or in conjunction with) a HV switch driver circuit for high voltage isolation, as will be described in greater detail below. Any of the pulse transformers 300 described herein may be configured as a multi-core pulse transformer that includes a first and second transformer core arranged in parallel, as shown in FIG. 3. In FIG. 3 two transformer cores 302, 302' of the pulse transformer 300 are shown. The two transformer cores may be placed on opposite sides (e.g., top and bottom sides) of a substrate 319, e.g., printed circuit board (PCB), on which the pulse generator circuitry, including the HV switch driver chip(s) 311 and HV switch/gate(s) 309 are arranged. The two cores shown in FIG. 3 (comprising two pulse transformers) are arranged in parallel, which may reduce the HV switch driver circuitry inductance.

Figure 3:
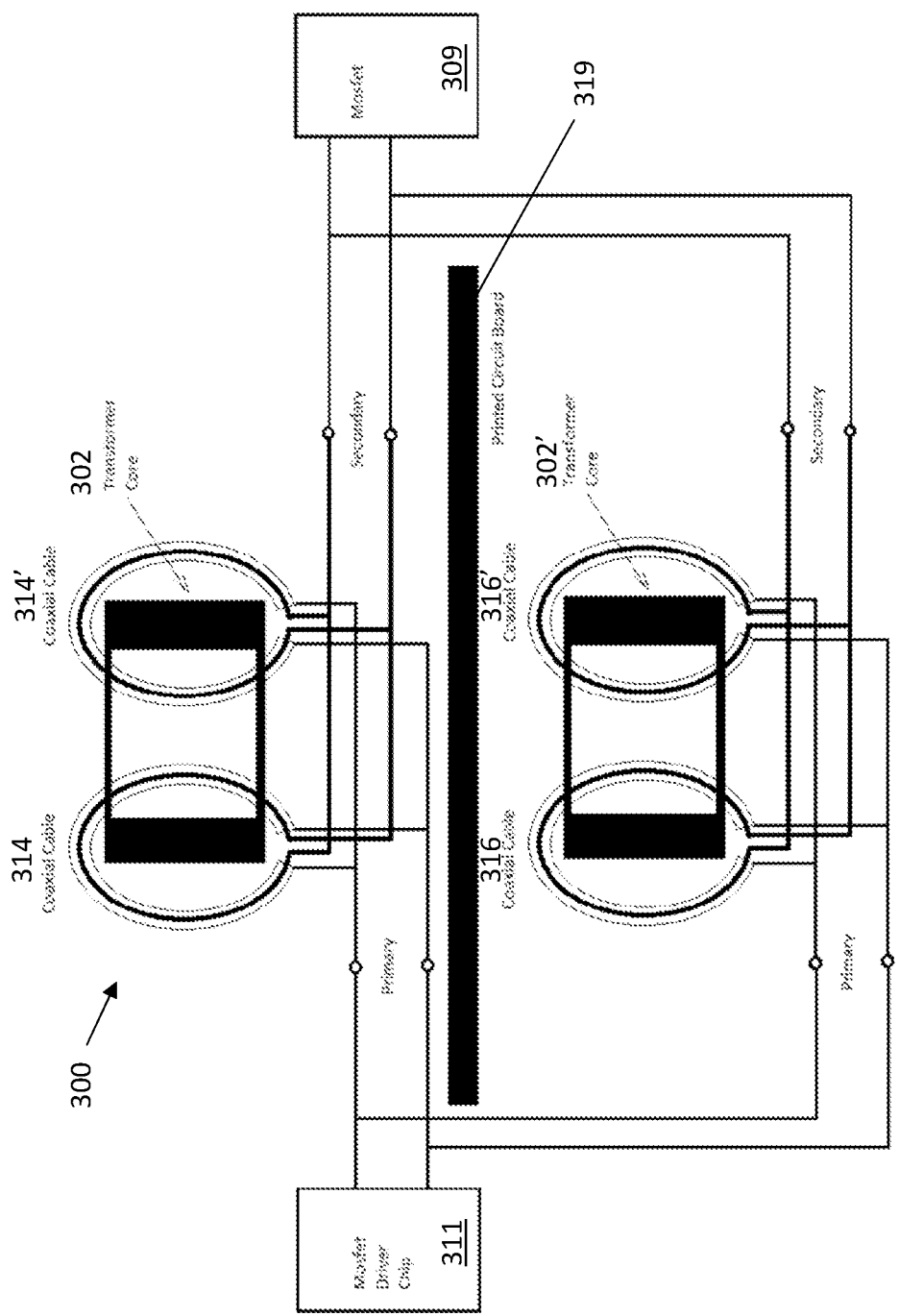
FIG. 3 is an example of two pulse transformers arranged in parallel each having an independent core wound with a plurality of cables connected in parallel between the MOSFET driver chip and the MOSFET (e.g., as part of the MOSFET gate driver). This configuration may be referred to collectively as a multi-core (e.g., dual-core) pulse transformer.
Figure 4:
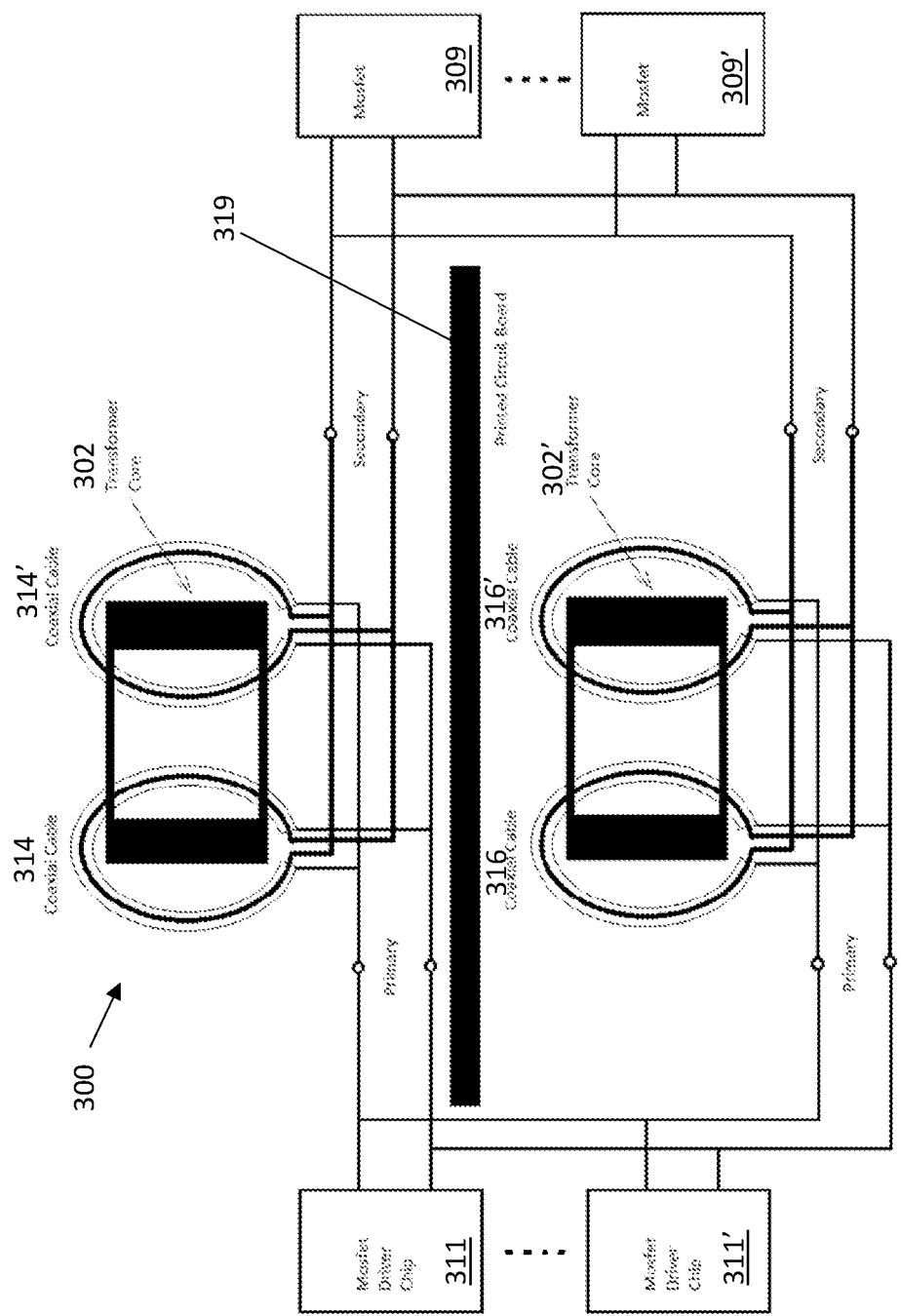
FIG. 4 is an example of a multi-core pulse transformer including two independent transformer cores that each have a plurality of coaxial cables (two are shown) forming primary and secondary windings in which the primaries are all electrically parallel and connected to a plurality of MOSFET drivers while the plurality of secondaries are all electrically parallel and connected to a plurality of MOSFETs.

In FIG. 3, the HV switch driver chip 311 is coupled to the primary winding of a pair of pulse transformers each including a transformer core 302, 302' and two (or in some cases more) coaxial cables configured as the primary and secondary windings. The coaxial cables forming the primary and secondary windings are arranged in parallel for each of the cores. A first pulse transformer is positioned on the first side of the substrate (e.g., the top of PCB 319) and includes a single core 302 and a pair of coaxial cables 314, 314' forming the primary and secondary windings that are electrically parallel. A second pulse transformer is positioned on the second side of the substrate (e.g., the bottom of PCB 319) and also includes a single core 302' and a pair of coaxial cables 316, 316' forming the primary and secondary windings that are electrically parallel with each other and with the primary and secondary windings in the first pulse transformer. The primary windings are connected to the HV switch driver chip 311 and the secondary windings are connected to the HV switch 309. Thus, FIG. 3 shows a dual-core pulse transformer including two independent cores 302, 302' arranged in parallel for a HV switch driver.

In some variations, multiple HV switch drivers (e.g., HV switch driver circuitry such as MOSFET driver chips) and/or multiple HV switches may be included and coupled to pulse transformers as shown. For example, FIG. 4 shows one variation in which two or more MOSFET driver chips 311, 311' are arranged in parallel and electrically connected via a dual-core pulse transformer having two independent cores 302, 302' arranged in parallel to two or more MOSFETs 309, 309'. In FIG. 4, all of the primary windings are arranged in parallel and electrically coupled to the outer coaxial conductor while the secondary windings are also all arranged in parallel and electrically coupled to the inner coaxial conductor; thus, the primary is arranged coaxially around the secondary winding.

The pulse transformers described herein may allow the use of smaller, multiple, pulse transformer cores that may provide a more compact implementation compared to cores with similar saturation that may otherwise need to be larger and more bulky, typically having a higher inductance. As shown in FIG. 4, at least two cores, arranged in parallel and independently, may be used. In some variations, more than two cores may be used and arranged in parallel, which may further avoid core saturation while decreasing the inductance of the coupling from the driver to the power HV switch (switching device, e.g., MOSFET).

Figure 5:
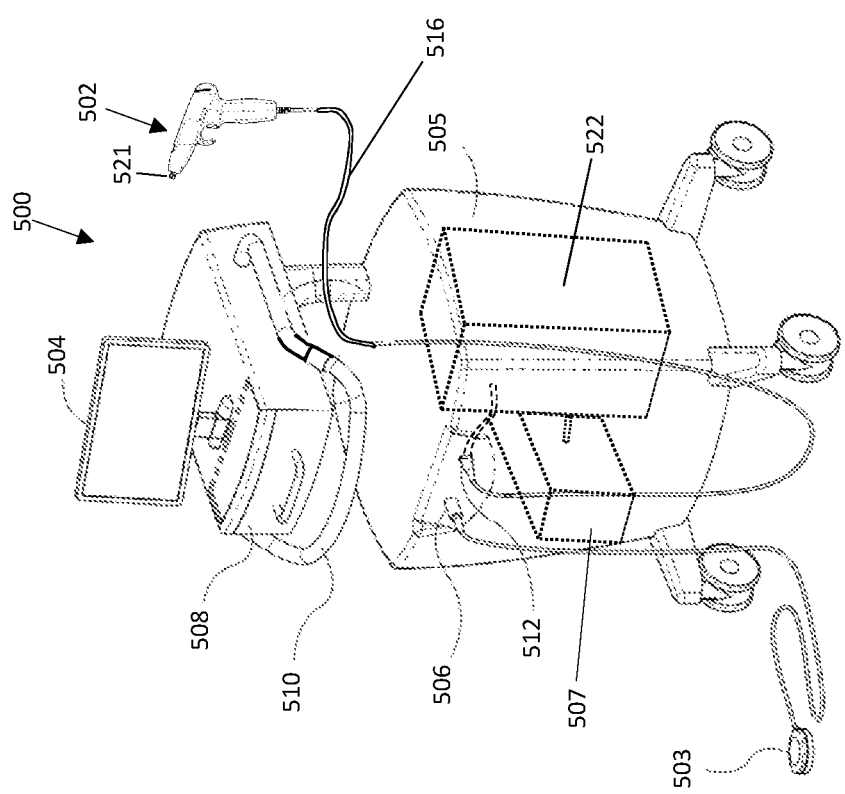
FIG. 5 is one example of an apparatus for delivering high voltage, short pulses of electrical energy, such as nanosecond pulsed electrical energy including a pulse transformer as described herein.

Any of the pulse transformers described herein may be particularly well suited for use as part of a pulse generator for treating a biological material (e.g., cells, tissue, etc.). For example, FIG. 5 illustrates one example of an apparatus for delivering sub-microsecond (e.g., nanosecond) pulsed electrical energy that includes a pulse generator configured to provide a high voltage pulsed output in the nanosecond range (e.g., less than 1000 ns). Examples of pulse generators that may include the pulse transformer(s) described herein may include those described in U.S. patent application Ser. No. 15/148,344 (published as US20170245928A1), filed on May 6, 2016, and U.S. Ser. No. 15/269,273 (published as US20180078755A1), which was filed on Sep. 19, 2016, and U.S. Ser. No. 15/595,684 (now U.S. Ser. No. 10/252, 050B2). Each of these patents and patent applications is herein incorporated by reference in its entirety herein.

In operation, a system including one or more pulse transformers may apply high voltage, nanosecond-duration pulse waveforms. The pulse transformer may further help reduce or eliminate arcing. FIG. 5 illustrates one example of a therapeutic apparatus for delivering nanosecond pulsed electrical energy that may include a pulse transformer as described herein. For example, described herein are apparatuses (e.g., nanosecond pulsed electrical fields (nsPEF) apparatuses) that may include one or more pulse transformers that may lower HV switch (e.g., MOSFET) driver circuit inductance. These apparatuses may be configured to provide pulse widths from 50 ns to 1 μs, having rise and fall-times, for example, of about 20 ns or less, pulse voltages as high as 1-15 kV (e.g., 10-15 kV, in some variations 18 kV or more). In some variations the pulse currents may be up to about 500 A (or greater). These apparatuses may be referred to herein as pulse generators or sub-microsecond pulse generators and may be a modified Marx high voltage pulse generator. This circuit/system architecture may include a plurality of HV switches that may be closed to deliver the nanosecond pulses over a transmission cable, and the HV switches may include (or be coupled with) one or more pulse transformers, such as a multi-core pulse transformer having at least two cores arranged in parallel. In an exemplary Marx high voltage pulse generator low-voltage pulse timing and triggering circuits may share common circuitry with system low voltage DC supply and system input control signals. Any of these apparatuses may include a multi-core (e.g., a dual-core) pulse transformer (having two or more independent cores) sharing parallel and, for example, coaxial primary and secondary windings connecting to one or more MOSFET drivers (e.g., MOSFET driver circuits or MOSFET driver chips) and one or more MOSFET(s).

FIG. 5 illustrates one example of an apparatus (e.g., a system) 500 for delivering high voltage, short pulses of electrical energy, such as nanosecond pulsed electrical energy, that includes a pulse generator 507 which may also include a multi-core pulse transformer.

In FIG. 5, the apparatus may include a pulse delivery output (e.g., configured as a handpiece 502) and the pulse generator 507, with one or more inputs (e.g., footswitch 503, and user interface 504). Footswitch 503 is connected to housing 505 through connector 506; the housing may enclose the electronic components, including the pulse generator 507 including the dual-core pulse transformers with parallel coaxial primary and secondary windings (not visible), and a fixed length of the transmission cable (inside the dashed outline 522). The handpiece 502 may include electrodes (e.g., a removable or swappable electrode tip 521) and connects to the pulse generator 507 circuitry through the transmission cable 516. The high voltage system 500 may also include a storage drawer 508, inputs (e.g., buttons, keyboard, etc.), and a monitor (user interface) 504. Additional circuitry (e.g., control circuitry, wireless circuitry, etc.) may be included as well. The system may also include a handle 510 and a faceplate 512.

A human operator may adjust one or more of the following settings of the system: the number of pulses, current or voltage amplitude, pulse duration, and pulse frequency, for example, by entering them into a numeric keypad or a touch screen of interface 504; alternatively or additionally, the user may select from one or more predefined protocols that include predetermined parameter settings. In some embodiments, the pulse width can be varied (e.g., within a defined range, such as between 1 ns and 1000 ns). A control unit or microcontroller (e.g., within the housing, not shown) may send signals to pulse control elements within the system 500.

In some variations, the apparatuses and methods described herein may be used for electroporation of biological material in a container (e.g., in a cuvette). The chamber, or cuvette, may be any appropriate size. For example, the container may be small and may have an electrical pulse impedance of −150. The electroporation pulse width may be in the nanosecond range and the voltage used can be many kV, such as 5 kV to 8 kV.

The apparatuses described herein may enable multi-kilovolt nanosecond pulses to be delivered to a cuvette.

As mentioned above, in many high voltage/high-power pulse generator designs the high voltage is rapidly switched from an energy storage circuit into a pulse generation path. A typical high voltage/high-power pulse generator example is the Marx generator, which is a designed to charge high voltage capacitors in parallel and then rapidly switch these charged capacitors to a series circuit that discharges through a different circuit than the charging circuit by switching MOSFETs using a gate driver. The apparatuses and methods described herein may help ensure high voltage isolation of the gate driver circuit and maintain a low circuit inductance. As described above, this may be accomplished by using the pulse transformers, e.g., multi-core pulse transformers arranged in parallel (and having parallel coaxial primary and secondary windings).

The pulse transformers described herein, and any pulse generators including them, may include the use of a primary and secondary winding, for example, coaxial as this configuration may be best for the parallel, dual-core pulse transformers described herein. The use of coaxial primary and secondary windings may reduce the leakage inductance of the pulse transformer. The arrangement of the primary and secondary may be switched (e.g., the primary may be coaxially arranged over the secondary or the secondary may be coaxially arranged over the primary). Generally, the coaxial arrangement may minimize leakage inductance and optimize coupling from primary to secondary. The coaxially cabling is generally selected so that its primary to secondary insulation rating is sufficiently high to prevent arcing or corona during operation of the apparatus, as the MOSFET (HV switch) banks (secondary) can be greater than about 5 kV (e.g., greater than about 1 kV, 5 kV, 10 kV, 12.5 kV, 15 kV, etc.) relative to the drive circuit (primary). In some variations it may be beneficial to minimize the length of the coaxial cabling, which may determine the coupling capacitance from primary to secondary. Typically the greater the length, the higher the primary to secondary capacitance and this can result in HV pulse feedback into the driver circuits, causing erratic pulsing and inducing MOSFET failures.

The use of multiple parallel transformers forming the (e.g., multi-core, such as dual-core) pulse transformers advantageously allow a lower inductance from the drive circuitry to the driven high voltage (HV) switches (e.g., MOSTFETs), while increasing the switch drive current without suturing the pulse transformer cores. More than two pulse transformers may be arranged in parallel. A pulse generator (such as the pulse generator shown in FIG. 5) may include a plurality of drivers (e.g., MOSFET drivers) that are triggered by a trigger input. Pairs of MOSFET drivers may be coupled to a bank of MOSFETs (e.g., 3, 4, 5, 6, etc. MOSFETS; more or fewer MOSFETS may be used) by a multi-core and parallel pulse transformer ("dual pulse transformer). Two drivers may be coupled to each MOSFET bank through each multi-core pulse transformer. The MOSFETs may be arranged in parallel for increased output current. In this example, the output of each the MOSFET bank may be coupled to a protection circuit.

The dual-core pulse transformer in this example may be similar to that shown in FIG. 4, in which a pair of cores is arranged in parallel and symmetrically about opposite sides of the printed circuit board.

The shape, size or type of the transformer core may be varied. In the variations described herein, which may be configured to provide a particularly compact pulse generator, the transformer cores may be configured to be sufficiently small so that they do not increase the spacing between the MOSFET (HV switch) banks, yet be sufficiently large such that they do not quickly saturate, reducing primary to secondary coupling.

A prototype circuit for a pulse generator implementing the pulse transformer may include a plurality of dual-core pulse transformers as part of the pulse generator board, with one core of each dual-core pulse transformer on the front side and the parallel core for each dual-core pulse transformer on the opposite side of the circuit substrate (e.g., printed circuit board). This may allow the board to remain in contact while increasing the MOSFET drive capability due to the parallel pulse transformers. The first side of the PCB (e.g., top side) may include an array of MOSFET switches, arranged in three stages for each of seven banks, e.g., in some variations with four FETs per bank. The top-side half of the dual-core pulse transformers may be positioned between the MOSFETS and the MOSFET drivers (two per MOSFET bank), as shown. The bottom-side half of the dual-core pulse transformers may be opposite from a top-side half. The top-side half and bottom-side half may be arranged in parallel, on either side of the PCB, minimizing the distance that the windings (coaxial cable forming the primary and secondary windings) must traverse to connect between the MOSFET drivers and MOSFETs. In some variations, pairs of MOSFET drivers may connect to the top-side core of a plurality of dual-core pulse transformers, which may in turn coupled to the MOSFETs. The MOSFETs may be arranged as a multi-bank stack of MOSFET switches with multiple MOSFETs (e.g., 3, 4, 5, 6, etc.) in parallel per bank. The MOSFETS may, in turn, be coupled to parallel protection circuits.

In operation, the dual-core pulse transformers described herein may result in a lower circuit inductance, increased speed for turning on/off the MOSFETs (and/or reducing delay times) and faster load arcing protection, due to the parallel configuration of the multiple cores, and in some variations the use of coaxial windings. This may result in a lower driving point inductance (e.g., at the MOSFET driver outputs) and higher drive current to the MOSFETs.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An apparatus for delivering pulsed electrical energy comprising:
   one or more multi-core pulse transformers, each multi-core pulse transformer comprising a first transformer core and a second transformer core, wherein the first transformer core includes one or more cables forming primary and secondary windings and the second transformer core includes one or more cables forming primary and secondary windings, wherein the primary windings of the first transformer core are coupled to the primary windings of the second transformer core and the secondary windings of the first transformer core are coupled to the secondary windings of the second transformer core;
   one or more high voltage switch drivers coupled to the primary windings of the first transformer core and the primary windings of the second transformer core; and
   one or more high voltage switches coupled to the secondary windings of the first transformer core and the secondary windings of the second transformer core,
   wherein the first transformer core and the second transformer core are arranged electrically in parallel between the one or more high voltage switch drivers and the one or more high voltage switches.

2. The apparatus of claim 1, wherein the one or more high voltage switches are MOSFETs and the one or more high voltage switch drivers are MOSFET drivers.

3. The apparatus of claim 2, wherein the one or more MOSFET drivers are coupled to the primary windings so that each primary winding is electrically parallel, and wherein the one or more MOSFETs are coupled to the secondary windings so that each secondary winding is electrically parallel.

4. The apparatus of claim 1, wherein the first transformer core is independent from the second transformer core.

5. The apparatus of claim 1, wherein the first transformer core is on a first side of a printed circuit board (PCB) to which the one or more high voltage switch drivers and the one or more high voltage switches are attached.

6. The apparatus of claim 5, wherein the second transformer core is on a second side of the PCB opposite from the first side.

7. The apparatus of claim 1, wherein the one or more cables forming the primary and/or secondary windings of the first transformer core are wound between 1 and 5 times around the first transformer core.

8. The apparatus of claim 1, wherein the primary windings and the secondary windings of the first transformer core are coaxially arranged relative to each other.

9. The apparatus of claim 1, wherein the primary windings and the secondary windings of the second transformer core are coaxially arranged relative to each other.

10. The apparatus of claim 1 configured as a part of a pulse generator system.

11. The apparatus of claim 10, wherein the pulse generator system comprises a pulse generator and a handpiece, wherein the handpiece is configured to deliver a high voltage pulsed output produced by the pulse generator.

12. The apparatus of claim 11, wherein the handpiece comprises a removable tip having a plurality of electrodes.

13. The apparatus of claim 1, wherein at least one of the one or more multi-core pulse transformers comprises more than 2 transformer cores.

14. An apparatus for delivering pulsed electrical energy comprising:
   one or more high voltage switch drivers;
   one or more high voltage switches; and
   one or more multi-core pulse transformers, each multi-core pulse transformer comprising a first transformer core and a second transformer core on opposite sides of a substrate, wherein the first transformer core and the second transformer core each include one or more cables forming primary and secondary windings, wherein the primary windings of the first transformer core are coupled to the primary windings of the second transformer core and the secondary windings of the first transformer core are coupled to the secondary windings of the second transformer core,
   wherein the one or more high voltage switch drivers are coupled to the primary windings such that each primary winding is electrically parallel to other primary windings, and the one or more high voltage switches are coupled to the secondary windings such that each secondary winding is electrically parallel to other secondary windings.

15. The apparatus of claim 14, wherein each primary winding is between the one or more high voltage switch drivers and the one or more high voltage switches.

16. The apparatus of claim 14, wherein each secondary winding is between the one or more high voltage switch drivers and the one or more high voltage switches.

17. The apparatus of claim 14, wherein the apparatus is configured to keep each of the first transformer core and the second transformer core below saturation to reduce an inductance and increase a switch drive current.

18. The apparatus of claim 16, wherein the secondary windings are coaxially arranged relative to the primary windings.

19. The apparatus of claim 14, wherein a high voltage pulsed output comprises nanosecond pulses.

20. A method of generating a pulsed output, the method comprising:
    emitting a driving pulse from a high voltage switch driver to a multi-core pulse transformer through a primary winding of a first transformer core and a primary winding of a second transformer core, wherein the primary winding of the first transformer core is coupled to the primary winding of the second transformer core and a secondary winding of the first transformer core is coupled to a secondary winding of the second transformer core; and
    receiving the driving pulse at a high voltage switch from the secondary winding of the first transformer core and the second transformer core.

21. The method of claim 20, wherein the pulsed output is in a nanosecond range.

22. The method of claim 20, wherein the high voltage switch is a MOSFET and the high voltage switch driver is a MOSFET driver, and wherein the MOSFET, MOSFET driver and the first transformer core are on a first side of a substrate, and the second transformer core is on a second side of the substrate directly opposite from the first transformer core.

23. The method of claim 20, further comprising emitting the driving pulse through a plurality of primary windings that are arranged in parallel.

24. The method of claim 20, wherein receiving comprises receiving the driving pulse at the high voltage switch from the secondary winding that is arranged coaxially relative the primary winding around the first transformer core and the second transformer core.

25. The method of claim 20, wherein the first transformer core and the second transformer core are arranged in parallel on either side of a substrate so that a circuit inductance is lowered sufficiently to reduce driving point inductance at high voltage switch driver outputs.

* * * * *